United States Patent [19]
Terada et al.

[11] 4,266,023
[45] May 5, 1981

[54] GLYCEROL OXIDASE AND PROCESS FOR THE PRODUCTION THEREOF AND METHOD FOR THE QUANTITATIVE DETERMINATION OF GLYCEROL BY GLYCEROL OXIDASE

[75] Inventors: Osamu Terada; Takayuki Uwajima; Akira Mihara; Kazuo Aisaka, all of Machida; Hiroko Akita, Yokohama; Toshiaki Nagai; Yoshiaki Shimizu, both of Shizuoka, all of Japan

[73] Assignee: Kyowa Hakko Kogyo Co., Ltd., Tokyo, Japan

[21] Appl. No.: 95,517

[22] Filed: Nov. 19, 1979

Related U.S. Application Data

[62] Division of Ser. No. 897,695, Apr. 19, 1978, Pat. No. 4,202,941.

[30] Foreign Application Priority Data

Apr. 19, 1977 [JP] Japan .................................. 52-44146

[51] Int. Cl.³ .......................... C12Q 1/28; C12Q 1/26
[52] U.S. Cl. ........................................ 435/28; 435/25; 435/817
[58] Field of Search ...................... 435/25, 27, 28, 190

[56] References Cited

PUBLICATIONS

Journal of General Microbiology (1978), vol. 107, pp. 289–296.
Annual Review of Microbiology (1976), vol. 30, pp. 535–578.

Primary Examiner—Lionel M. Shapiro
Attorney, Agent, or Firm—Craig & Antonelli

[57] ABSTRACT

Glycerol oxidase is an oxidizing enzyme of glycerol characterized by its ability to oxidize glycerol in the presence of oxygen to form hydrogen peroxide and glyceraldehyde. This enzyme is produced by cultivation of a microorganism belonging to the genus Aspergillus or the genus Neurospora in a nutrient medium.

4 Claims, 11 Drawing Figures

GLYCEROL OXIDASE AND PROCESS FOR THE PRODUCTION THEREOF AND METHOD FOR THE QUANTITATIVE DETERMINATION OF GLYCEROL BY GLYCEROL OXIDASE

This is a division of application Ser. No. 897,695, filed Apr. 19, 1978 now U.S. Pat. No. 4,202,941, issued May 13, 1980.

This invention relates to an oxidizing enzyme of glycerol, which will be hereinafter referred to as "glycerol oxidase", a process for producing this oxidizing enzyme, and a novel method for the quantitative determination of glycerol by the use of the glycerol oxidase.

In accordance with the present invention, a novel enzyme, glycerol oxidase, and a novel method for the quantitative determination of glycerol by said enzyme are first provided.

The present inventors have made various studies of enzymes using various microorganisms belonging to the genus Aspergillus and the genus Neurospora. As a result, the inventors have found that there is an enzyme in the culture broth obtained by culturing microorganisms, such as *Aspergillus joponicus* KY-45; *Neurospora crassa* KY-462, etc. The present inventors have investigated properties of the enzyme, have found that the enzyme is a new enzyme which selectively oxidizes glycerol, and have named the enzyme "glycerol oxidase".

Heretofore, such a new enzyme has been in demand but its presence has not been confirmed.

The novel enzyme provided according to the process of the present invention has the following enzymological and physicochemical properties:

(1) Action:

The present glycerol oxidase oxidizes glycerol under the consumption of oxygen to form hydrogen peroxide and glyceraldehyde.

(2) Substrate specificity:

The present enzyme reacts very specifically with glycerol.

(3) Optimum pH and stable pH range:

(3.1) Optimum pH;

Glycerol oxidase produced by the microorganisms of the genus Aspergillus (which will be hereinafter referred to as "enzyme of the genus Aspergillus"): pH 7–8

Glycerol oxidase produced by the microorganisms of the genus Neurospora (which will be hereinafter referred to as "enzyme of the genus Neurospora"): pH 8.0–8.5

(3.2) Stable pH range:

Enzyme of the genus Aspergillus: pH 5.0–8.0
Enzyme of the genus Neurospora: pH 5.0–8.0

(4) Method for the determination of the enzyme activity:

The enzyme activity is expressed by "unit." A "unit" of the enzyme activity is defined as that amount of enzyme which will decompose 1μ mole of glycerol at 37° C. in 1 minute in the presence of oxygen. The determination of the enzyme activity is carried out as follows: glycerol is reacted with glycerol oxidase with stirring to form hydrogen peroxide, and 4-aminoantipyrine and phenol are reacted with the resulting hydrogen in the presence of peroxidase to derive quinoneimine pigment. The optical density at 500 nm of the resulting uinoneimine pigment is measured to determine the amount of generated hydrogen peroxide, whereby the enzyme activity is determined (which will be hereinafter referred to as "4-AA method").

In the present invention, specific activity is defined by unit per 1 mg of protein. The amount of the enzyme protein is measured according to Lowry method using copper-Folin reagent [O. H. Lowry, N.J. Rosebrough, A. L. Farr and R. J. Randall: J. Biol. Chem., 193, 265 (1951)].

(5) Optimum temperature range for action:

Enzyme of the genus Aspergillus: about 40° C.
Enzyme of the genus Neurospora: 40°–45° C.

(6) Conditions for Inactivation by pH, temperature, etc.:

(6.1) Condition for Inactivation by temperature:

Enzyme of the genus Aspergillus is inactivated about 60% after treatment at 45° C. for 30 minutes and substantially inactivated after treatment at 60° C. for 30 minutes.

Enzyme of the genus Neurospora is inactivated about 50% after treatment at 25° C. for 30 minutes and substantially inactivated after treatment at 50° C. for 30 minutes.

(6.2) Condition for Inactivation by pH:

Enzyme of the Aspergillus is inactivated at a pH value of above 10 or below 4 for 30 minutes.

Enzyme of the genus Neurospora is inactivated at a pH the same as above indicated.

(7) Inhibition, activation and stabilization:

(7.1) Inhibitor:

Enzymes activities obtained by adding 1 mM of various inhibitors are shown in Table 1, the activity of the enzyme with no addition of the inhibitor being defined as 100. The activities are measured according to 4-AA method deriving a pigment of 4-aminoantipyrine system from the generated $H_2O_2$.

TABLE 1

| Inhibitor | Enzyme of the genus Aspergillus | Enzyme of the genus Neurospora |
|---|---|---|
| None | 100 | 100 |
| $AgNO_3$ | 30 | — |
| $HgCl_2$ | 20 | 23 |
| $Pb(CH_3COO)_2$ | 15 | — |
| $CuSO_4$ | 10 | 20 |
| $ZnSO_4$ | — | 23 |
| $FeSO_4$ | — | 0 |
| $NaN_3$ | 20 | — |
| 0-phenanthroline | 90 | — |
| α,α'-dipyridyl | 85 | — |
| PCMB (p-chloromercuribenzoate) | 50 | 108 |
| N-ethylmaleimide | 100 | — |
| $NH_2OH$—HCl | 0 | 0 |
| 8-hydroxyquinoline | 90 | — |
| diethyldithiocarbamate | 35 | 20 |
| neocuproine | 100 | — |
| iodoacetate | — | 100 |
| cysteine | — | 60 |
| dithiothreitol | 100 | — |
| EDTA | 105 | 80 |

(7.2) Activation:

No compound has been found yet especially for the activation.

(7.3) Stabilization:

Enzyme of the genus Aspergillus can be stabilized by adding 0.1 mM to 1.0 mM of a sulfhydryl compound such as mercaptoethanol, dithiothreitol, etc. thereto.

(8) Method for purification:

Purification can be carried out according to the following conventional procedures: (1) fractional precipitation by ammonium sulfate, (2) column chromatography on DEAE cellulose, (3) sieving fractionation by Sephadex, (4) column chromatography on hydroxyapatite, (5) freeze-drying of active fractions, etc. as will be hereinafter described in detail.

(9) Molecular weight:

The molecular weight of the present enzyme is determined according to the elution pattern by analysis using Sephadex G-200 column. As the result, the enzyme of the genus Aspergillus is determined to have a molecular weight of 300,000 or more.

(10) Crystal structure and elemental analysis:

No crystallization has been succeeded yet, and no determination has been made yet.

It has been clarified that the enzyme provided according to the present invention is a novel enzyme having the foregoing properties, that is, glycerol oxidase.

Now, a novel process for producing the enzyme and a process for purifying the same provided according to the present invention will be described in detail below.

Glycerol oxidase can be obtained by culturing a microorganism having an ability to produce glycerol oxidase and belonging to the genus Aspergillus or the genus Neurospora in a nutrient medium containing an appropriate carbon source, nitrogen source, inorganic materials and other nutrients, and recovering glycerol oxidase from the resulting culture broth.

Any microorganism can be used, so long as it belongs to the genus Aspergillus or the genus Neurospora, and has an ability to produce glycerol oxidase. As suitable microorganisms, *Aspergillus japonicus* KY-45 (FERM-P No. 3959, NRRL 11102), *Aspergillus oryzae* KY-63 (NRRL 11103), *Aspergillus parasiticus* KY-77 (NRRL 11104), *Aspergillus flavus* KY-98 (NRRL 11105), *Neurospora crassa* KY-462 (FERM-P NO. 3960, NRRL 11106), *Neurospora sitophila* KY-445 (NRRL 11264), *Neurospora tetrasperma* KY-447 (NRRL 11265), etc. can be mentioned.

Microbiological properties of these microorganisms are disclosed in the following literatures:

| | |
|---|---|
| *Aspergillus japonicus*: | The genus Aspergillus: The Williams & Wilkins Co., Baltimore, 1965, P. 327-328 |
| *Aspergillus oryzae*: | ibid, p. 370-373 |
| *Aspergillus parasiticus*: | ibid, p. 369-371 |
| *Aspergillus flavus*: | ibid, p. 361-365 |
| *Neurospora crassa*: | Comparative Morphology of Fungi, McGraw-Hill Book Company, Inc., New York and London 1928, p. 227; Jour. Agr. Res., 34, p. 1019-1042 (1927) |
| *Neurospora sitophila*: | ibid, p. 226-227 |
| *Neurospora tetrasperma*: | ibid, p. 227 |

Any of synthetic medium and natural medium can be used as a medium in the present invention, so long as it properly contains a carbon source, nitrogen source, inorganic materials and other nutrients.

As the carbon source, carbohydrates such as glucose, blackstrap molasses, etc., and sugar alcohols such as glycerol, sorbitol, mannitol, etc. can be used.

As the nitrogen source, ammonia, various inorganic and organic ammonium compounds such as ammonium chloride, ammonium sulfate, ammonium carbonate, ammonium phosphate, ammonium acetate, etc., nitrogen compounds such as urea, etc., nitrogenous organic materials such as peptone, yeast extract, casein hydrolyzate, defatted soybeans, or the digested products thereof, etc., can be used.

As the inorganic materials, salts of such metals as sodium, potassium, manganese, magnesium, calcium, cobalt, nickel, zinc, copper, etc., and salts of chromium, sulfuric acid, phosphoric acid, nitric acid, hydrochloric acid, etc., can be used.

In the present invention, glycerol oxidase can be obtained in best yield, when a glycerol oxidase producing microorganism is cultured in a medium containing glycerol. For example, productivity of glycerol oxidase in terms of activity obtained when the microorganism is cultured in a medium containing glycerol is 10 to 100 times as high as that obtained when the microorganism is cultured in a medium containing 1 g/dl glucose, 1 g/dl malt extract and 0.5 g/dl yeast extract or the Czapeck medium.

It is preferable that 0.1 to 5 g/dl of glycerol is added to a medium.

Culturing is usually carried out at a temperature of 20° to 40° C., preferably 25° to 35° C., and at a pH of 6 to 8 at the start of culturing, preferably at about 7. A considerable amount of glycerol oxidase is formed in the resulting culture broth by shaking culture or aeration-agitation submerged culture under said conditions for 30 to 72 hours.

Glycerol oxidase thus formed in the resulting culture broth can be recovered in the following manner:

Since glycerol oxidase is usually formed in the microbial cells, the procedure for recovering the enzyme from the microbial cells is described below. Microbial cells obtained by filtration or centrifugation of culture broth after the completion of culturing are sufficiently washed with water or buffer solution. Then, the microbial cells are suspended in an appropriate amount of a buffer solution, and disrupted. Disruption is carried out by mechanical disintegration [for example, by mortar, Dyno-mill (product of Willy A. Bachofen, Switzerland), Manton goulin, French press, Fuse press, ultrasonic disintegrator, etc.].

Solid mterials are removed from the resulting solution of the disrupted microbial cells by filtration or centrifugation, and then glycerol oxidase is recovered from the solution according to the conventional procedure for isolating enzymes. For example, enzyme powders can be obtained according to steps of (1) fractional precipitation with ammonium sulfate, (2) column chromatography on DEAE cellulose, (3) sieve fractionation by Sephadex, (4) column chromatography on hydroxyapatite, and (5) freeze-drying of active fractions. Of course, repetition of the same operating steps, and other conventional purification methods can be used in combination, if required.

Enzymological and physico-chemical properties of glycerol oxidase thus obtained are described below (as glycerol oxidase, the respective purified preparates obtained in Examples 1 and 2, are used).

I. Action

The enzyme specifically oxidizes glycerol under the consumption of oxygen to form hydrogen peroxide and glyceraldehyde.

(a) Confirmation of formation of hydrogen peroxide:

(a)-1. Glycerol oxidase is reacted with glycerol in the presence of oxygen, and then peroxidase, phenol and 4-aminoantipyrine are added to the enzyme system, whereby quinoneimine pigment is formed in the reaction system [reaction of hydrogen peroxide with peroxidase, phenol and 4-aminoantipyrine is disclosed in Clin. Chem. 20, p. 470 (1974)].

(a)-2. Glycerol oxidase is reacted with glycerol in the presence of oxygen to form hydrogen peroxide, and catalase is added to decompose the generated hydrogen peroxide. Then, peroxidase, phenol and 4-aminoantipyrine are added to the reaction system to conduct the same reaction as above, but the same quinoneimine pigment is not formed in the reaction system.

(a)-3. When catalase is presented in the glycerol oxidation system catalyzed by glycerol oxidase in the presence of oxygen, the amount of oxygen uptake is decreased to half. This fact is supported by the following experimental facts:

(a)-3-1. Reaction composition A (system free from catalase):

| Reagents | |
|---|---|
| Aqueous 0.01M glycerol solution | 0.5 ml |
| 0.1M NH$_4$OH–NH$_4$Cl buffer solution (which will be hereinafter referred to as "ammonium buffer solution") (pH 8.0) | 1.0 ml |
| Aqueous glycerol oxidase solution | 0.2 ml *1 |
| Aqueous 2.4 mM 4-aminoantipyrine solution | 0.5 ml |
| Aqueous 42 mM phenol solution | 0.5 ml |
| Aqueous peroxidase solution | 0.2 ml *2 |
| Water | 0.1 ml |

*1 5 μ moles of glycerol oxidase having a specific activity of 30 obtained in Example 1 of the present invention.
*2 Made by Sigma Corp. (U.S.A.), containing 200 units of specific activity of 1,000.

(a)-3-2. Reaction Composition B (system containing catalase):

| Reagents | |
|---|---|
| Aqueous 0.01M glycerol solution | 0.5 ml |
| 0.1M ammonium buffer solution (pH 8.0) | 1.0 ml |
| Aqueous glycerol oxidase solution | 0.2 ml *1 |
| Aqueous catalase solution | 1.0 ml *3 |
| Water | 0.3 ml |

*1 Same as in Reaction Composition A
*3 Made by Sigma Corp. (U.S.A.), containing 100 units of catalase having a specific activity of 100.

Figure 1:
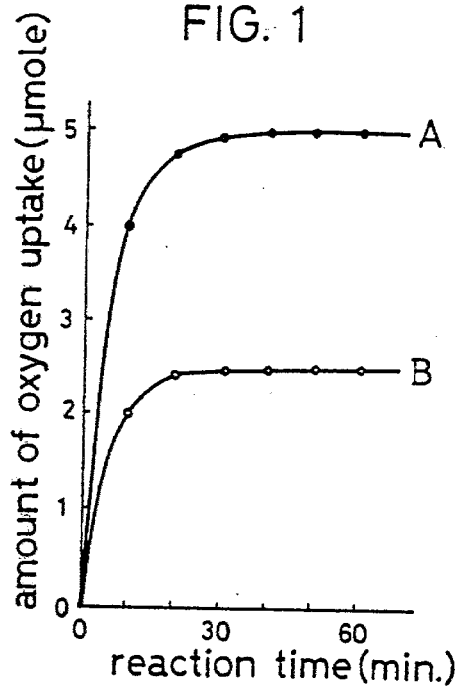
FIG. 1 shows the amount of oxygen uptake in a reaction system where glycerol oxidase is reacted with glycerol in the presence of oxygen. In this figure, curve A represents the amount of the oxygen uptake in the reaction system free from catalase and curve B the amount of the oxygen uptake in the presence of catalase.

(a)-3-3. Reaction operation:

In case of the system free from catalase, the reagents shown in Reaction Composition A are mixed, and reaction is carried out at 37° C. with stirring. The amount of oxygen uptake is measured by a Warburg's manometer. The results are shown in FIG. 1.

In case of the system containing catalase, the reagents shown in Reaction Composition B are mixed, and reaction is carried out at 37° C. Similarly, the amount of oxygen uptake is measured, and is shown in FIG. 1. As is evident from FIG. 1, 4.95μ moles of oxygen is consumed in the absence of catalase (curve A in FIG. 1) for 5.0μ moles of glycerol as a substrate.

In the presence of catalase (curve B in FIG. 1), 2.49μ moles of oxygen is consumed, which is equal to about one-half of that of (A).

It is confirmed from the foregoing reaction systems (a)-1, (a)-2 and (a)-3 that the present enzyme can form hydrogen peroxide.

Quantitative determination of the generated hydrogen peroxide is made by colorimetric quantitative determination of the formed quinoneimine pigment. That is, it is confirmed by the quantitative determination of the formed hydrogen peroxide in the system of Reaction Composition A according to 4-AA method that 4.92μ moles of hydrogen peroxide is formed from 5μ moles of glycerol.

(b) Confirmation of formation of glyceraldehyde:

(b)-1. Glycerol oxidase is reacted with glycerol in the presence of oxygen, and a reaction product is identified to be glyceraldehyde.

(b)-1-1. Procedure for identification:

(b)-1-1-(1). Reaction solution:

Five drops of an aqueous solution containing 50 mg/ml of glycerol, 5 drops of solution containing 10 u/ml of glycerol oxidase in 0.02 M Tris-HCl buffer solution, and 1 drop of 14,000 u/ml of catalase are collected, and reaction is carried out at 30° C. with shaking for 20 hours.

(b)-1-1-(2). Identification:

As a result of the thin layer chromatography given below (which will be hereinafter referred to as "TLC"), the product in the reaction solution is identified as glyceraldehyde by comparison with the authentic substance.

The thin layer plate used is silica gel G-60F-254 (trademark of E. Merck, West Germany), and developing solvents are solvent system 1 [butanol:acetic acid:- water=4:1:1 (by volume)], and solvent system 2 [butanol:pyridine:water=3:2:1.5 (by volume)].

After the development, three kinds of reactions, that is, p-anisidine hydrochloric acid reaction, periodic acid-benzidine reaction, and 2,4-dinitrophenylhydrazine reaction are conducted on the plate, and it is confirmed that Rf values of the reaction products and color tones of the spots formed by said reactions are identical with those of the authentic substances. The results are given in Table 2.

TABLE 2

Identification of reaction products by TLC
(Rf values and coloring reaction)

| coloring agent | Developing solvent sample | Solvent System 1 | Solvent system 2 |
|---|---|---|---|
| p-anisidine hydrochloric acid reagent[1] | Glyceraldehyde (authentic substance) | 0.67 Rf value (brown) | 0.76 (brown) |
| | Reaction product | Rf value 0.67 (brown) | 0.77 (brown) |
| Periodic acid-benzidine reagent[2] | Glyceraldehyde (authentic substance) | 0.66 Rf value (+)* | 0.76 (+)* |
| | Reaction product | 0.67 Rf value (+)* | 0.77 (+)* |
| 2,4-dinitrophenyl-hydrazine reagent[3] | Glyceraldehyde (authentic substance) | 0.67 Rf value (orange) | 0.77 (orange) |
| | Reaction product | Rf value 0.68 (orange) | 0.77 (orange) |

Color indicated in parentheses shows color tone of the spot, and (+)* in periodic acid-benzidine reagent means white spot in blue background.
Notes
[1]p-anisidine hydrochloric acid reagent: reductive carbonyl compounds such as sugars react with p-anisidine hydrochloric acid to exhibit coloration characteristic of respective structures.
[2]periodic acid-benzidine reagent: polyalcohol and compounds having a similar structure thereto consume periodic acid. Thus, those compounds are detected by a white spot.
[3]2,4-dinitrophenylhydrazine reagent: carbonyl compound reacts with 2,4-dinitrophenylhydrazine to form 2,4-dinitrophenylhydrazone, and is detected by an orange spot.

As shown in the foregoing table, the products and the glyceraldehyde authentic substance are completely identical with one another in the Rf values and coloration by the coloring reagents. Thus, it is confirmed that the product obtained by reaction of glycerol oxidase with glycerol in the presence of oxygen is glyceraldehyde.

(b)-2. The amount of glyceraldehyde formed when glycerol oxidase is reacted with glycerol in the presence of oxygen is almost equimolar to that of consumed glycerol. The fact is confirmed by adding 2,4-dinitrophenylhydrazine to the reaction system to prepare 2,4-dinitrophenylhydrazone of the product and quantitatively determining the latter product by colorimetry.

(c) Confirmation of the amount of oxygen uptake:

Consumption of oxygen in the system where glycerol oxidase is reacted with glycerol is measured by an oxygen electrode and a Warburg's manometer. As a result, it is confirmed that the amount of oxygen uptake meets with the amount of the formed glyceraldehyde.

(d) Quantitative determination of the amount of hydrogen peroxide, the amount of glyceraldehyde and the amount of oxygen uptake are carried out according to the procedures described in the above three items (a), (b) and (c). As a result, it is found that those obtained data are stoichiometrically reasonable.

It is confirmed from said qualitative and quantitative experimental results that the present enzyme oxidizes glycerol to form hydrogen peroxide and glyceraldehyde according to the following equation, that is, that the present enzyme is glycerol oxidase.

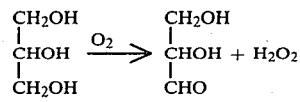

II. Substrate specificity

The relative activity is measured using other substrates in equimolar amounts to that of glycerol in the procedure for measuring the activity according to 4-AA method.

The relative activities on other substrates are given in Table 3, the activity on glycerol being defined as 100.

TABLE 3

| Substrate | Enzyme of the genus Aspergillus | Enzyme of the genus Neurospora |
|---|---|---|
| glycerol | 100 | 100 |
| 1,2-propanediol | 10.5 | 0 |
| 1,3-propanediol | 3.3 | 0 |
| 1,3-butanediol | 2.0 | 0 |
| Glycerol-3-phosphoric acid | 0.4 | 21 |
| 1,4-butanediol | 0.3 | 0 |
| 2,3-butanediol | 0.3 | 0 |
| ethanol | 0 | 0 |
| n-propyl alcohol | 0 | 0 |
| isopropyl alcohol | 0 | 0 |

III. Optimum pH and stable pH range

1. Optimum pH of enzyme of the genus Aspergillus is in a range of 7 to 8.

Figure 2:
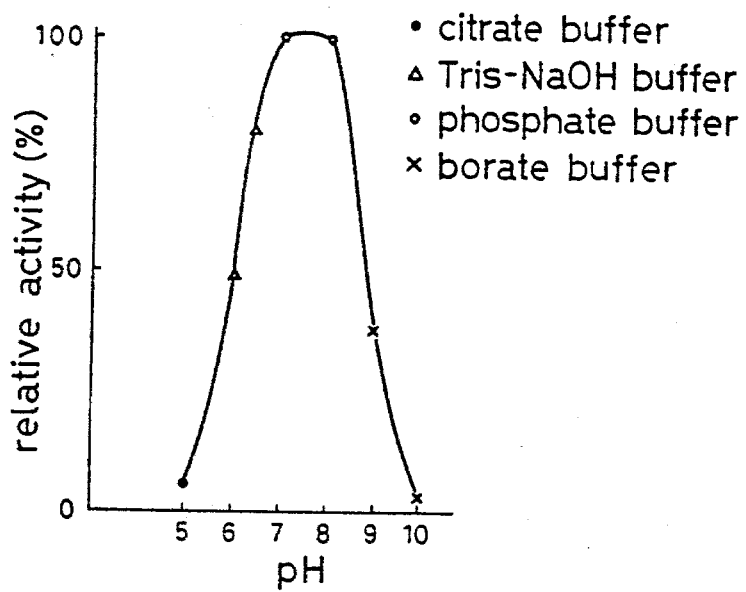
FIG. 2 shows relative activities of the enzyme of the genus Aspergillus after incubation at 37° C. and various pH for 10 minutes.

The activities are measured after incubation at 37° C. at various pH values for 10 minutes. The results are shown in FIG. 2.

2. Stable pH range of enzyme of the genus Aspergillus is 5.0 to 8.0.

Figure 3:
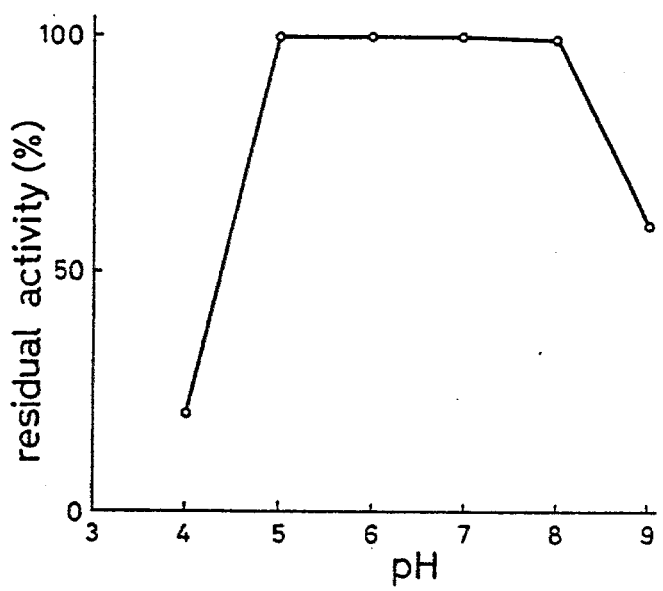
FIG. 3 shows residual activities of the enzyme of the genus Aspergillus after treatment at 30° C. and various pH for 30 minutes.

Residual activities are measured after treatment at 30° C. and various pH for 30 minutes, using the following buffer solutions. The results are shown in FIG. 3.

Note:
pH 4–5: Acetate buffer solution is used.
pH 6–7: Tris-HCl buffer solution is used.
pH 8–9: Borate buffer solution is used.

3. Optimum pH of enzyme of the genus Neurospora is 8.0 to 8.5.

Figure 4:
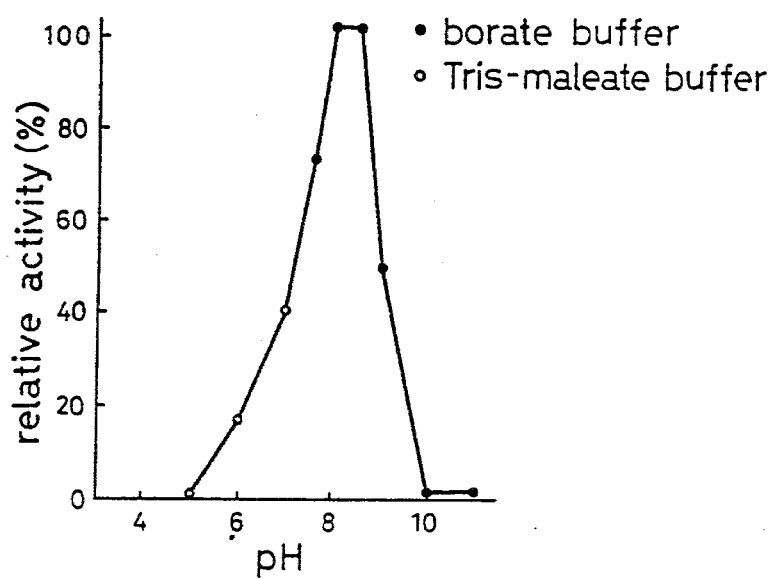
FIG. 4 shows relative activities of the enzyme of the genus Neurospora after incubation at 37° C. and various pH for 10 minutes.

Activity is measured after incubation at 37° C. and various pH for 10 minutes. The results are shown in FIG. 4.

Figure 5:
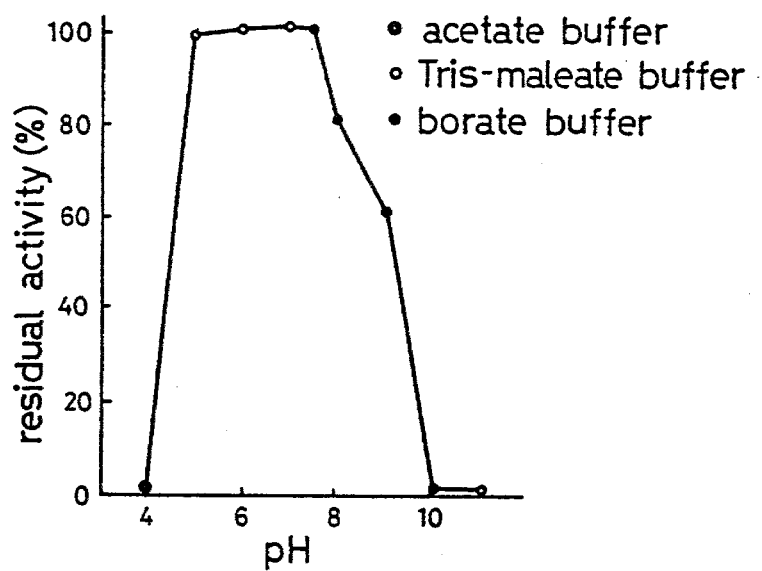
FIG. 5 shows residual activities of the enzyme of the genus Neurospora after treatment at 30° C. and various pH for 30 minutes.

4. Stable pH range of enzyme of the genus Neurospora is 5 to 8.0. Measurement is carried out in the same manner as in the foregoing item III-2. The results are shown in FIG. 5.

IV. Procedure for determination of the enzyme activity (a) Principle:

Determination of the enzyme activity is carried out by reacting hydrogen peroxide generated by the enzyme with 4-aminoantipyrine and phenol in the presence of peroxidase to obtain quinoneimine pigment, and quantitatively determining the resulting quinoneimine pigment.

Reaction formulae are given by the following equations (1) and (2):

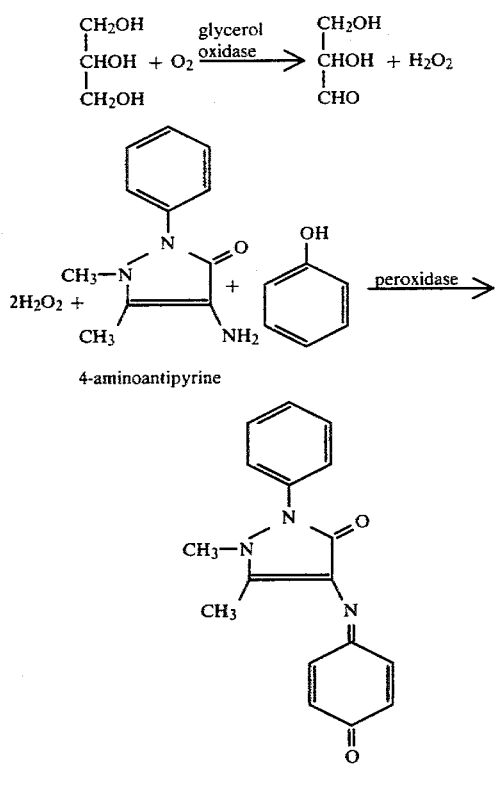

Reaction principle of equation (2) is disclosed by C. C. Allain et al.: Clin Chem. 20, 470 (1974).

(b) Reagents:

| (1) | Substrate: aqueous 0.1M glycerol solution | 0.5 ml |
|---|---|---|
| (2) | Buffer solution: 0.1M ammonium buffer solution (pH 8) | 1.0 ml |
| (3) | 4-Aminoantipyrine: aqueous 2.4 mM solution | 0.5 ml |
| (4) | Phenol: 42 mM (aqueous solution) | 0.5 ml |
| (5) | Aqueous peroxidase solution: (Amount of protein: 2 mg/ml, Specific activity: 100) | 0.1 ml |
| (6) | Water | 0.3 ml |
| (7) | Aqueous enzyme solution | 0.1 ml |

(c) Operational procedure:

The reagents (1)–(6) are mixed in a test tube, and then shaken at 37° C. for 5 minutes. Then, enzyme solution is added thereto, and thus obtained mixture is made up to 3 ml with ammonium buffer solution. Reaction is carried out at 37° C. for 10 minutes with shaking. On the other hand, similar procedure is repeated using water in place of the test solution as a reference. The optical density of the reaction solution at 500 mm is measured, and a difference from the control is determined as ΔOD (optical density).

(d) Calculation of the enzyme activity:

One unit of glycerol oxidase is the amount of the enzyme which will decompose 1μ mole of glycerol at 37° C. in 1 minute.

On the other hand, the absorption coefficient of 0.5 mM of quinoneimine pigment is reported as 5.33 [Clin Chem. 20, 470 (1974)], and thus, if the optical density (ΔOD) at 500 nm of 3 ml of the reaction solution obtained according to the foregoing operational procedure IV-(c) is represented by a, the desired enzyme activity (A) per milliliter of the enzyme solution is calculated from the following formula:

$$A = a \times \frac{1}{5.33} \times 3 \times \frac{1}{10}$$
$$= a \times 0.56 \text{ (units/ml)}$$

Figure 6:
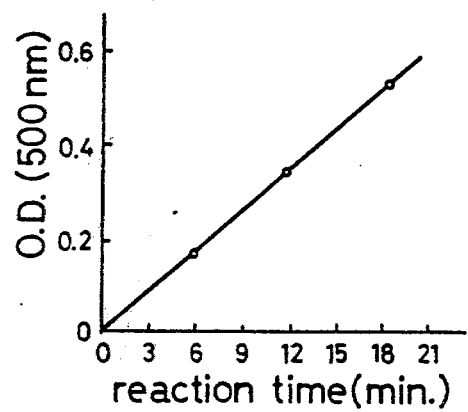
FIG. 6 shows relation between reaction time and OD value (at 500 nm) in measuring the activity of the enzyme.

OD values at 500 nm of reaction solutions are measured by changing the reaction time in the measurement of the enzyme activity, and the results shown in FIG. 6 are obtained.

It is evident from FIG. 6 that the OD values at 500 nm are proportional to the reaction times.

Figure 7:
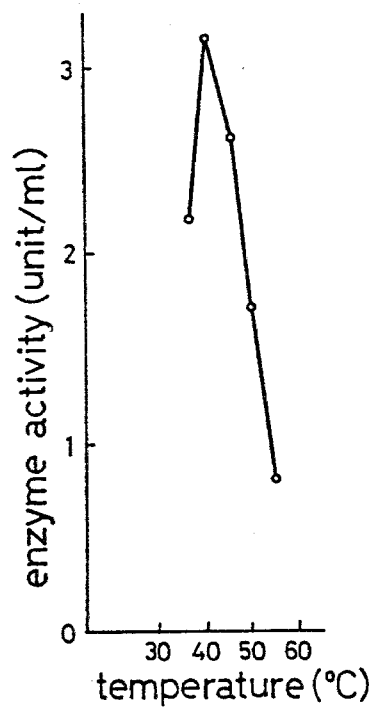
FIG. 7 shows the enzyme activities of the enzyme of the genus Aspergillus after incubation at pH 8 and various temperatures for 10 minutes.

V. Optimum temperature range for action (1) Enzyme of the genus Aspergillus:

The enzyme activities after incubation at pH 8 and various temperatures for 10 minutes are shown in FIG. 7. The optimum temperature is at about 40° C.

Figure 8:
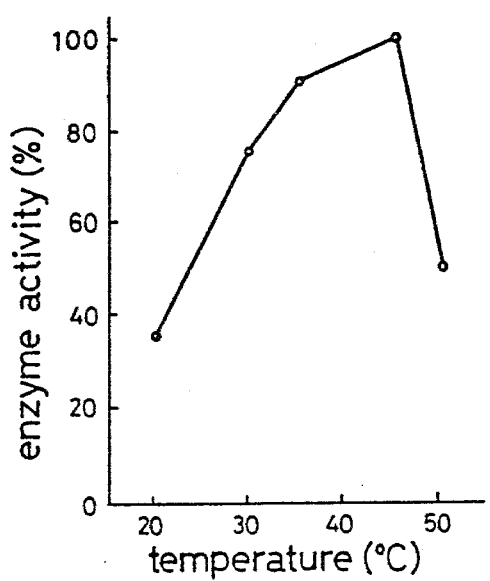
FIG. 8 shows the enzyme activities of the enzyme of the genus Neurospora after incubation at pH 8 and various temperatures for 10 minutes.

(2) Enzyme of the genus Neurospora:

The enzyme activities after incubation at pH 8 and various temperatures for 10 minutes are shown in FIG. 8. The optimum temperature is at about 35° to 45° C.

VI. Inactivation conditions by pH, temperature, etc.

Inactivation by pH condition:

As described in the foregoing item III on the optimum pH and stable pH range, the enzyme of the genus Aspergillus is substantially 100% inactivated below pH 4 or above pH 10. Similarly, the enzyme of the genus Neurospora is substantially 100% inactivated below pH 4 or above pH 10.

Inactivation by temperature:

Residual activity is measured after heat treatment at pH 7.0 for 30 minutes in 0.1 M Tris-HCl buffer solution.

Figure 9:
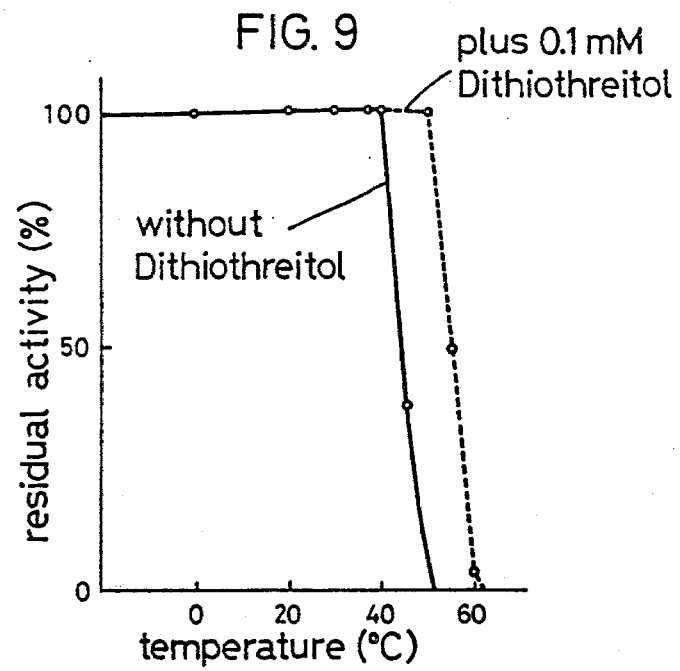
FIG. 9 shows residual activities of the enzyme of the genus Aspergillus after treatment at pH 7 and various temperatures in 0.1 M ammonium buffer solution for 30 minutes.
Figure 10:
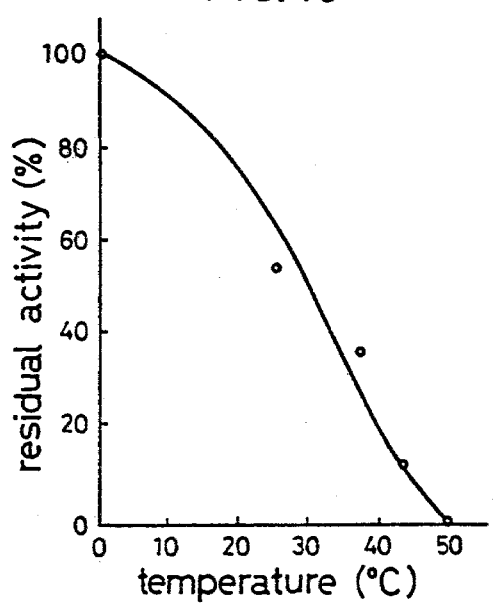
FIG. 10 shows residual activities of the enzyme of the genus Neurospora after treatment at pH 7 and various temperatures in 0.1 M ammonium buffer solution for 30 minutes.

The results as to the enzyme of the genus Aspergillus are shown in FIG. 9, and those as to the enzyme of the genus Neurospora in FIG. 10. The former is 100% stable up to 40° C., but is about 60% inactivated at 45° C. The latter is about 50% inactivated at 30° C. and about 100% inactivated at 50° C. The former (the enzyme of the genus Aspergillus) is stabilized by addition of 0.1 mM dithiothreitol, and its thermal resistance is also increased (see FIG. 9 where it is stable up to about 50° C.).

Now, a method for the quantitative determination of glycerol by the novel enzyme, glycerol oxidase, provided according to the present invention is described below.

The following methods are available for the quantitative determination of glycerol:

(a) A method which comprises reacting glycerol oxidase with glycerol in the presence of oxygen, and quantitatively determining the formed hydrogen peroxide.

(b) A method which comprises reacting glyceraldehyde which is formed in the above (a) with 2,4-dinitrophenylhydrazine, forming 2,4-dinitrophenylhydrazone, quantitatively determining the 2,4-dinitrophenylhydrazone by colorimetry, and thereby quantitatively determining glycerol.

(c) A method which comprises reacting glycerol oxidase with glycerol in the presence of oxygen, and measuring an amount of oxygen uptake of the system.

The principles and the procedures of the methods (a), (b) and (c) are described in the above item I. However, as an example, the method (a) for the quantitative determination of glycerol by measuring the amount of the formed hydrogen peroxide will be described below:

The optical density of reaction solutions at 500 nm is determined according to the operational procedure described in the foregoing item IV-(c), using solutions containing 0.1 mg of the enzyme having a specific activity of 3.2 per milliliter of the solutions changing the concentration of the substrate (glycerol) solution to 0.1 mM, 0.2 mM, 0.5 mM, 1.0 mM, 5.0 mM, and 10.0 mM in the foregoing item IV-(b). The results are shown in Table 4.

TABLE 4

| Substrate cocentration OD value | 0.1 mM | 0.2mM | 0.5mM | 1.0mM | 5.0mM | 10.0mM |
| --- | --- | --- | --- | --- | --- | --- |
| OD value at 500 nm | 0.060 | 0.121 | 0.303 | 0.605 | 3.002 | 5.998 |

It is observed that there is a linear relationship between the substrate concentration (glycerol concentration) and the OD value of reaction solutions at 500 nm. On the basis of this principle, glycerol contained in solution at an unknown concentration can be quantitatively determined.

Thus, the glycerol concentration of a solution can be measured using glycerol oxidase. This fact will suggest a new procedure and kit for the quantitative determination of glycerol or derivatives thereof.

A method for the quantitative determination of glycerol has been in demand, for example, in the field of biochemistry. Various methods are known for the quantitative determination of triglyceride by hydrolyzing triglyceride in serum to form glycerol and fatty acid, and measuring the glycerol.

As the chemical method for the quantitative determination of glycerol, chromotropic acid method, acetylacetone method, triazole method, Randrup method, and Mendelsohn fluorescense method are known, but all those methods have such a disadvantage that the reactions in those methods are non-specific to glycerol.

As the enzyme method, a method using glycerokinase (E.c.2.7.1.30) is known, but the reaction must be conducted together with pyruvate kinase (E.c.2.7.1.40) and lactate dehydrogenase (E.c.1.1.1.27), and thus it takes much time in the measurement and consequently the method is unsuitable for the treatment of a large number of samples.

It has been found that the present glycerol oxidase directly oxidizes glycerol to form hydrogen peroxide stoichiometrically. Thus, the obtained hydrogen peroxide is easily converted to a coloring system, and quantitative determination of glycerol, that is, quantitative determination of triglyceride can be very simply and specifically made by the colorimetrical quantitative determination.

Now, the present invention will be described in detail below, referring to examples.

EXAMPLE 1

*Aspergillus japonicus* KY-45 (ATCC 1042, NRRL 11102, FERM-P No. 3959) is inoculated in 300 ml of seed medium containing 10 g/l of glycerol, 10 g/l of malt extract, and 5 g/l of yeast extract (pH 6.2 before sterilization) in a 2-l Erlenmeyer flask, and cultured at 30° C. with shaking for 48 hours. Nine hundred milliliters (corresponding to three flasks) of the resulting seed culture is inoculated in 15 l of the same medium as said seed medium in a 30-l jar fermenter, and cultured at 30° C. with aeration (15 l/min.) and stirring (250 rpm) for 40 hours. After the culturing, the resulting culture broth is filtered through a Buchner funnel, and the cakes are washed with water, whereby about 150 g (dry basis) of microbial cells is obtained.

The microbial cells are suspended in 5 l of 10 mM ammonium buffer solution (pH 8.0), and disrupted in Dyno-mill (made by Willy A. Bachofen, Switzerland). After the disruption, the disrupted suspension is centrifuged by a freezing centrifuge (20,000×G for 20 minutes), and 4.7 l of supernatant (protein content: 51 g, specific activity: 0.05 units/mg) is obtained. The resulting supernatant is admixed with ammonium sulfate, and fractions precipitated at 30–70% saturation with ammonium sulfate are collected, and dissolved in 50 ml of 10 mM ammonium buffer solution (pH 8.0). The resulting solution is dialyzed against 10 l of 10 mM ammonium buffer solution, using a cellophane tube as a dialysis membrane.

Dialysis is continued for 48 hours with total of 40 l of dialysis solution, while exchanging the dialysis solution at every 12 hours. Dialyzed enzyme solution is passed through a column (5.5×40 cm) of DEAE cellulose (made by Serva Co., West Germany) equilibrated in advance with 10 mM ammonium buffer solution (pH 8.0). Enzyme is adsorbed through said operation, and unadsorbed impure protein is washed out with the same buffer. Then, the elution is carried out by a linear gradient of 0.1 M to 0.2 M ammonium sulfate in 2 l of 10 mM ammonium buffer solution (pH 8.0), whereby glycerol oxidase is eluted. Five hundred milliliters of the active fractions (protein content: 1.2 g, specific activity 1.1) are collected, and admixed with ammonium sulfate to make 70% saturation and to precipitate the enzyme.

Then, precipitates are collected by centrifugation (20,000×G for 20 minutes), and dissolved in 50 ml of 10 mM ammonium buffer solution (pH 8.0). The solution is passed through a column (5.5×80 cm) of Sephadex G-100 (made by Pharmacia Fine Chemicals, Co., Sweden) equilibrated in advance with 10 mM ammonium buffer solution (pH 8.0). One liter of 10 mM ammonium buffer solution (pH 8.0) is passed through the column and eluate is obtained in fractions. From the fractions, 300 ml of a fraction having a high specific activity (protein content: 310 mg, specific activity: 3.2) is obtained, and admixed with ammonium sulfate to make 70% saturation and to precipitate enzyme. Then, the precipitates are collected by centrifugation (20,000×G for 20 minutes) and dissolved in 20 ml of 10 mM ammonium buffer solution (pH 8.0). The resulting solution is dialyzed for 24 hours against 5 l of 10 mM ammonium buffer solution (pH 8.0), using a cellophane tube as a dialysis membrane, while twice exchanging the dialysis solution. After the dialysis, the resulting enzyme solution is passed through a column (5.5×20 cm) of hydroxyapatite equilibrated in advance with 10 mM ammonium buffer solution (pH 8.0). Furthermore, 250 ml of the same buffer is passed through the column, and eluate is obtained in fractions. Fractions having a specific activity higher than 20 are collected, and freeze-dried, whereby 10.2 mg of purified powdery enzyme preparate of glycerol oxidase (specific activity: 30.2) is obtained. The purified enzyme has a specific activity about 610 times as high as that of cell extract. The yield is 19% in terms of activity.

EXAMPLE 2

In place of *Aspergillus japonicus* KY-45 of Example 1, *Neurospora crassa* KY-462 (NRRL 11106, FERM-P No. 3960) is inoculated in five 2-1 Erlenmeyer flasks containing 10 g/l of glycerol, 10 g/l of malt extract, and 5 g/l of yeast extract and cultured at 30° C. for 48 hours with shaking in the same manner as in Example 1.

The resulting culture broth is extracted and purified in the same manner as in Example 1, whereby 1.1 mg of purified enzyme preparate of glycerol oxidase (specific activity: 14.1) is obtained in a 10.5% yield in terms of activity.

EXAMPLE 3

In this example, the procedure in Example 1 is repeated except that five strains shown in Table 5 are used in place of *Aspergillus japonicus* KY-45. The glycerol oxidase activities of the resulted supernatant of cell extract are shown in Table 5.

TABLE 5

| Strains | Activity u/l |
| --- | --- |
| *Aspergillus oryzae* KY 63 (NRRL 11103) | 320 |
| *Aspergillus parasticus* KY 77 (NRRL 11104) | 216 |
| *Aspergillus flavus* KY 98 (NRRL 11105) | 108 |
| *Neurospora sitophila* KY 445 (NRRL 11264) | 325 |
| *Neurospora tetrasperma* KY 447 (NRRL 11265) | 105 |

EXAMPLE 4

(a) Reagents to be used:

| | | |
| --- | --- | --- |
| (1) | Test solution: aqueous glycerol solution (concentration: unknown) | 0.5 ml |
| (2) | Buffer solution: 0.1M ammonium buffer solution (pH 8) | 1.0 ml |
| (3) | 4-aminoantipyrine: aqueous 2.4 mM solution | 0.5 ml |
| (4) | Phenol: aqueous 42 mM solution | 0.5 ml |
| (5) | Peroxidase: aqueous peroxidase solution (protein content: 20 mg/ml, specific activity: 1000) | 0.1 ml |
| (6) | Water | 0.3 ml |
| (7) | Enzyme: Glycerol oxidase obtained in Example 1 (protein content: 1.0 mg/ml, specific activity: 3.2) | 0.1 ml |

(b) Procedure:

The above reagents (1)–(6) are placed in a test tube, and shaken sufficiently at 37° C. for 5 minutes. Then, an enzyme solution is added thereto, and thus obtained reaction mixture is made up to 3 ml with ammonium buffer solution. Reaction is conducted at 37° C. for 10 minutes with shaking.

On the other hand, similar procedure is repeated using water in place of the test solution as a reference.

Figure 11:
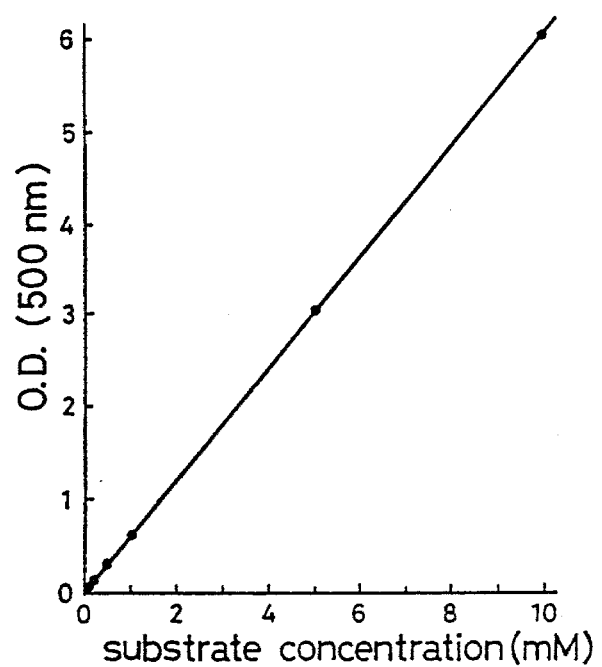
FIG. 11 shows relation between substrate (glycerol) concentration and optical density of reaction solutions at 500 nm in Table 4.

The OD value at 500 nm of the test solution is measured, and a difference $\Delta$OD from the reference is 0.230. From the working curve of FIG. 11, glycerol content in the test solution is determined to be 0.380 mM.

What is claimed is:

1. A method for the quantitative determination of glycerol in solution which comprises reacting glycerol oxidase, an enzyme having the ability to oxidize glycerol in the presence of oxygen to form hydrogen peroxide and gylceraldehyde, with the glycerol in the presence of oxygen and measuring the amount of oxygen consumed, or the amount of hydrogen peroxide or glyceraldehyde formed in an aqueous medium by the action of said glycerol oxidase, said amount being an indication of the concentration of glycerol in said solution.

2. The method of claim 1, wherein the formed hydrogen peroxide is quantitatively determined by reacting the peroxide with 4-aminoantipyrine and phenol in the presence of peroxidase to obtain quinoneimine pigment, which is quantitatively determined by measuring the optical density of the reaction solution at 500 nm.

3. The method of claim 1, wherein the glyceraldehyde formed is reacted with 2,4-dinitrophenylhydrazine, to form 2,4-dinitrophenylhydrazone and the 2,4-dinitrophenylhydrazone is quantitatively determined by colorimetry, this providing a quantitative determination of glycerol.

4. The method of claim 1, wherein the amount of oxygen consumed is measured by an oxygen electrode and a Warburg's manometer.

* * * * *